United States Patent
Langan et al.

(10) Patent No.: US 11,972,850 B2
(45) Date of Patent: Apr. 30, 2024

(54) HANDS-FREE MEDICATION TRACKING

(71) Applicant: CareFusion 303, Inc., San Diego, CA (US)

(72) Inventors: John Langan, Carlsbad, CA (US); Evan Chen, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/009,695

(22) PCT Filed: Jun. 9, 2021

(86) PCT No.: PCT/US2021/036542
§ 371 (c)(1),
(2) Date: Dec. 9, 2022

(87) PCT Pub. No.: WO2021/252580
PCT Pub. Date: Dec. 16, 2021

(65) Prior Publication Data
US 2023/0238098 A1 Jul. 27, 2023

Related U.S. Application Data

(60) Provisional application No. 63/038,054, filed on Jun. 11, 2020.

(51) Int. Cl.
*G16H 20/10* (2018.01)
*G06F 3/01* (2006.01)
(Continued)

(52) U.S. Cl.
CPC ............ *G16H 20/10* (2018.01); *G06F 3/012* (2013.01); *G06T 19/00* (2013.01); *G06V 10/70* (2022.01);
(Continued)

(58) Field of Classification Search
CPC ......... G06F 3/011; G06F 3/012; G06Q 50/22; G06T 19/00; G06T 19/006;
(Continued)

(56) References Cited

U.S. PATENT DOCUMENTS 8,743,244 B2 * 6/2014 Vartanian ............... H04N 23/63
348/333.02
9,215,293 B2 * 12/2015 Miller ..................... G06F 3/016
(Continued)

FOREIGN PATENT DOCUMENTS

| EP | 2732761 A1 | 5/2014 |
|---|---|---|
| EP | 2732761 A1 | 5/2014 |

(Continued)

OTHER PUBLICATIONS

International Search Report of International Application No. PCT/US2021/036542, dated Sep. 16, 2021, 4 pages.
(Continued)

*Primary Examiner* — Chun-Nan Lin
(74) *Attorney, Agent, or Firm* — Morgan, Lewis & Bockius LLP

(57) ABSTRACT

The disclosed systems and methods provide hands-free medication tracking. A method includes providing an augmented reality device attachable to a face of a user. The method also includes determining, using one or more sensors of the augmented reality device, a user action to be carried out with respect to a medication. The method also includes presenting, via a display interface of the augmented reality device, a visual indicator to assist with the user action. The method also includes confirming, via the one or more sensors of the augmented reality device, a completion of the user action. The method also includes sending, via a communication interface of the augmented reality device, an update message to a server indicating the completion of the
(Continued)

user action, wherein the update message causes the server to update a medication inventory in a database.

20 Claims, 7 Drawing Sheets

(51) Int. Cl.
    *G06T 19/00*         (2011.01)
    *G06V 10/70*         (2022.01)
    *G06V 20/20*         (2022.01)
    *G06V 40/19*         (2022.01)
    *G16H 40/20*         (2018.01)

(52) U.S. Cl.
    CPC .............. *G06V 20/20* (2022.01); *G06V 40/19* (2022.01); *G16H 40/20* (2018.01); *G06T 2210/41* (2013.01)

(58) Field of Classification Search
    CPC ............. G06T 2200/24; G06T 2210/41; G06T 2219/004; G06V 10/70; G06V 20/20; G06V 40/19; G16H 20/10; G16H 20/13; G16H 20/17; G16H 40/20; G16H 40/63; G16H 40/67
    See application file for complete search history.

(56) References Cited

U.S. PATENT DOCUMENTS

| | | | |
|---|---|---|---|
| 9,224,096 B2 | 12/2015 | Oppenheimer | |
| 9,836,907 B2 | 12/2017 | Phillips et al. | |
| 10,288,881 B2 | 5/2019 | Christensen | |
| 10,726,370 B1 | 7/2020 | Bernacki et al. | |
| 11,297,285 B2* | 4/2022 | Pierce | A61C 1/084 |
| 11,436,829 B2* | 9/2022 | Cork | G06F 3/167 |
| 11,594,313 B1* | 2/2023 | Satapathy | G16H 40/67 |
| 2012/0316897 A1* | 12/2012 | Hanina | G16H 40/67 705/3 |
| 2013/0169781 A1* | 7/2013 | Hanina | G16H 30/40 348/77 |
| 2015/0209113 A1 | 7/2015 | Burkholz et al. | |
| 2016/0270656 A1* | 9/2016 | Samec | A61B 3/1241 |
| 2018/0365385 A1* | 12/2018 | Cooney | G16H 20/60 |
| 2019/0035499 A1* | 1/2019 | Daya | G16H 20/10 |
| 2019/0164394 A1* | 5/2019 | Visitacion | G06F 3/016 |
| 2019/0251354 A1* | 8/2019 | Cork | G16H 40/63 |
| 2020/0160057 A1 | 5/2020 | Roxas et al. | |
| 2021/0038088 A1* | 2/2021 | Atallah | A61B 3/112 |
| 2021/0342591 A1 | 11/2021 | Cork et al. | |
| 2022/0044772 A1* | 2/2022 | Moghadam | A61B 5/7455 |

FOREIGN PATENT DOCUMENTS

| | | |
|---|---|---|
| WO | 2015175681 A1 | 11/2015 |
| WO | WO-2015175681 A1 | 11/2015 |

OTHER PUBLICATIONS

International Preliminary Report on Patentability from the Preliminary Examining Authority for Application No. PCT/US2021/036542, dated Aug. 12, 2022, 20 pages.

International Search Report and Written Opinion for Application No. PCT/US2021/036542, dated Sep. 16, 2021, 16 pages.

Written Opinion from the International Preliminary Examining Authority for Application No. PCT/US2021/036542, dated May 20, 2022, 9 pages.

* cited by examiner

HANDS-FREE MEDICATION TRACKING

CROSS-REFERENCE TO RELATED APPLICATION(S)

This application claims priority to U.S. provisional application Ser. No. 63/038,054, entitled "HANDS-FREE MEDICATION TRACKING," filed on Jun. 11, 2020, the entirety of which is incorporated herein by reference.

TECHNICAL FIELD

The present disclosure generally relates to augmented reality devices, and more specifically relates to methods and systems for providing hands-free medication tracking using an augmented reality device.

BACKGROUND

To track medications and manage inventory, users may use handheld devices and paper documentation. For example, handheld barcode scanners may be used to scan barcode labels affixed to medications, invoices, or other paperwork. The medications can then be identified based on the scanned barcodes, thereby facilitating inventory management. However, these handheld devices require the use of one or more hands, which may impede healthcare workflow processes wherein hands are preferably made free for holding charts, tablets, medical devices, and other items. Further, handheld devices may be tethered to a specific location or device, limiting deployment flexibility and user mobility. Inventory updates based on paper documentation may also facilitate transcription errors, document misplacement, and medication diversion. Accordingly, there is a need for improved systems and methods of medication tracking.

SUMMARY

According to various implementations, a method for providing hands-free medication tracking using an augmented reality device is provided. The method may include providing an augmented reality device attachable to a face of a user. The method may also include determining, using one or more sensors of the augmented reality device, a user action to be carried out with respect to a medication. The method may also include presenting, via a display interface of the augmented reality device, a visual indicator to assist with the user action. The method may also include confirming, via the one or more sensors of the augmented reality device, a completion of the user action. The method may also include sending, via a communication interface of the augmented reality device, an update message to a server indicating the completion of the user action, wherein the update message causes the server to update a medication inventory. Other aspects include corresponding systems, apparatuses, and computer program products for implementation of the foregoing method.

According to various implementations, the subject technology includes a wearable augmented reality device comprising: a display interface for presenting a graphical user interface including at least one opaque or semi-transparent graphic element; a communication interface; a location sensor for detecting location information identifying a location of the wearable augmented reality device; an environment sensor for capturing information within the location; and a processor configured to: determine, using location information from the location sensor and environment information from the environment sensor, a user action to be carried out with respect to a medication; present, via the display interface, a visual indicator to assist with the user action; confirm, via information received from at least one of the location sensor or the environment sensor, a completion of the user action; and send, via the communication interface, an update message to a server indicating the completion of the user action, wherein the update message causes the server to update a medication inventory in a database. Other aspects include corresponding systems, methods, computer program products, and apparatuses for implementation of the foregoing device.

Other aspects include corresponding systems, apparatuses, and computer program products for implementation of the foregoing device and method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

DESCRIPTION

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

The subject technology provides an augmented reality device for hands-free medication tracking. A user wearing the augmented reality device may, for example, direct gaze towards a particular medication for identification by sensors of the device, such as front facing cameras. Besides identification of the medication, a user action with respect to the identified medication can also be determined. For example, an authenticated user identifier, a detected location, and/or data provided by the sensors can be used to determine the user action. User actions may include, for example, intake of medication from restock areas, retrieval of medication from automated dispensing machines, bins, or shelves, placement of medication into shelves or bins, administration of medication to a patient, and disposal of excess medications. After confirming a completion of the user action, an update message may be sent to a server to cause a corresponding inventory update, for example by updating quantities of medications in an inventory database. In this manner, medication inventory can be updated and built over time automatically by workers wearing the augmented reality device, thereby advantageously avoiding error-prone manual update processes.

Figure 1:
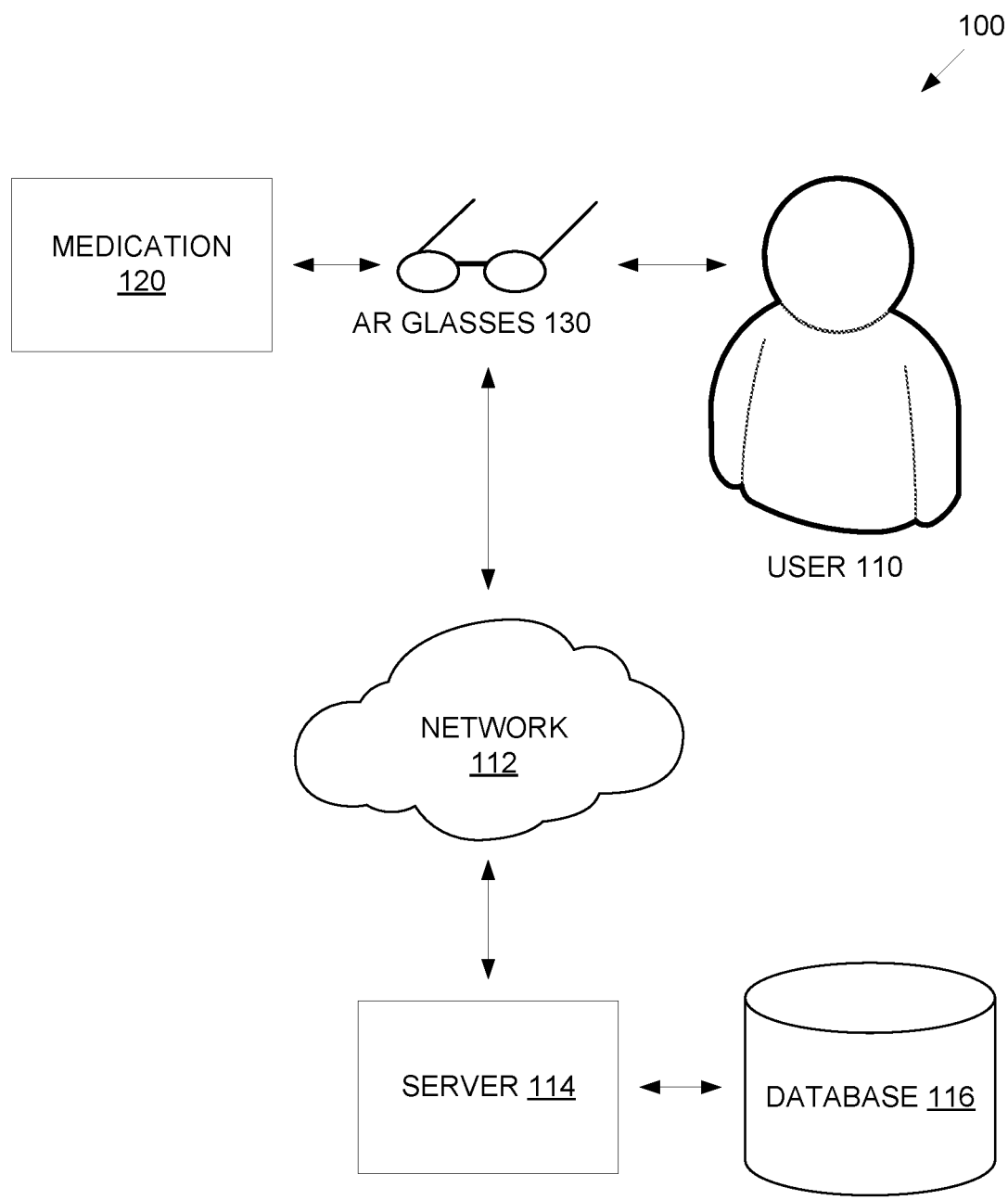
FIG. 1 depicts an example system for using an augmented reality device for hands-free medication tracking, according to various aspects of the subject technology.

FIG. 1 depicts an example system 100 including augmented reality (AR) glasses 130 for providing hands-free medication tracking, according to various aspects of the subject technology. Although the augmented reality device is shown as an integrated pair of glasses in FIG. 1, various other implementations may be provided, such as a clip-on module for attaching to existing glasses or other forms of eye-wear (e.g., goggles, face shields, and masks). User 110 may wear AR glasses 130 to track various medications, such as medication 120. To identify medication 120, sensors of AR glasses 130 may provide data for a lookup request to be sent to server 114 via network 112. The lookup request may include information such as location, viewing angle, images, video, audio, user identifier, user role identifier, and user eye tracking information. Server 114 may query database 116 to identify medication 120 based on the lookup request. Further, AR glasses 130 may determine and confirm a user action with respect to medication 120, such as adding, removing, administering, or disposing of medications. A message indicating the user action may then be sent to server 114 to cause an update in an inventory stored in database 116.

In some implementations, the inventory management may be performed while a user wearing the AR glasses 130 are performing another task. For example, a user is accessing a matrix drawer including several different storage locations (e.g., bins or pockets) for different items. While the AR glasses 130 may be used to authorize and track a user taking an item from a specific bin, data captured by the AR glasses 130 of bins near the specific bin may be used to track inventory of other items. In some implementations, the system may identify a discrepancy between the data captured by the AR glasses 130 and an inventory management system count for the item. After detecting a discrepancy, the system may adjust one or more device to confirm the inventory. For example, the dispensing cabinet may receive an instruction to require entry of a count for the bin before allowing a dispense event from the bin. As another example, AR glasses 130 worn by a pharmacy clinician, who may be responsible for maintaining the stock of items within the dispenser, may present augmentation information when the dispenser is identified in their field of view to indicate that a discrepancy was identified. The discrepancy may include inventory count, expiration, or other property of an item that can be detected or inferred from a correlation between data detected by the AR glasses 130 and a hospital information system.

Figure 2:
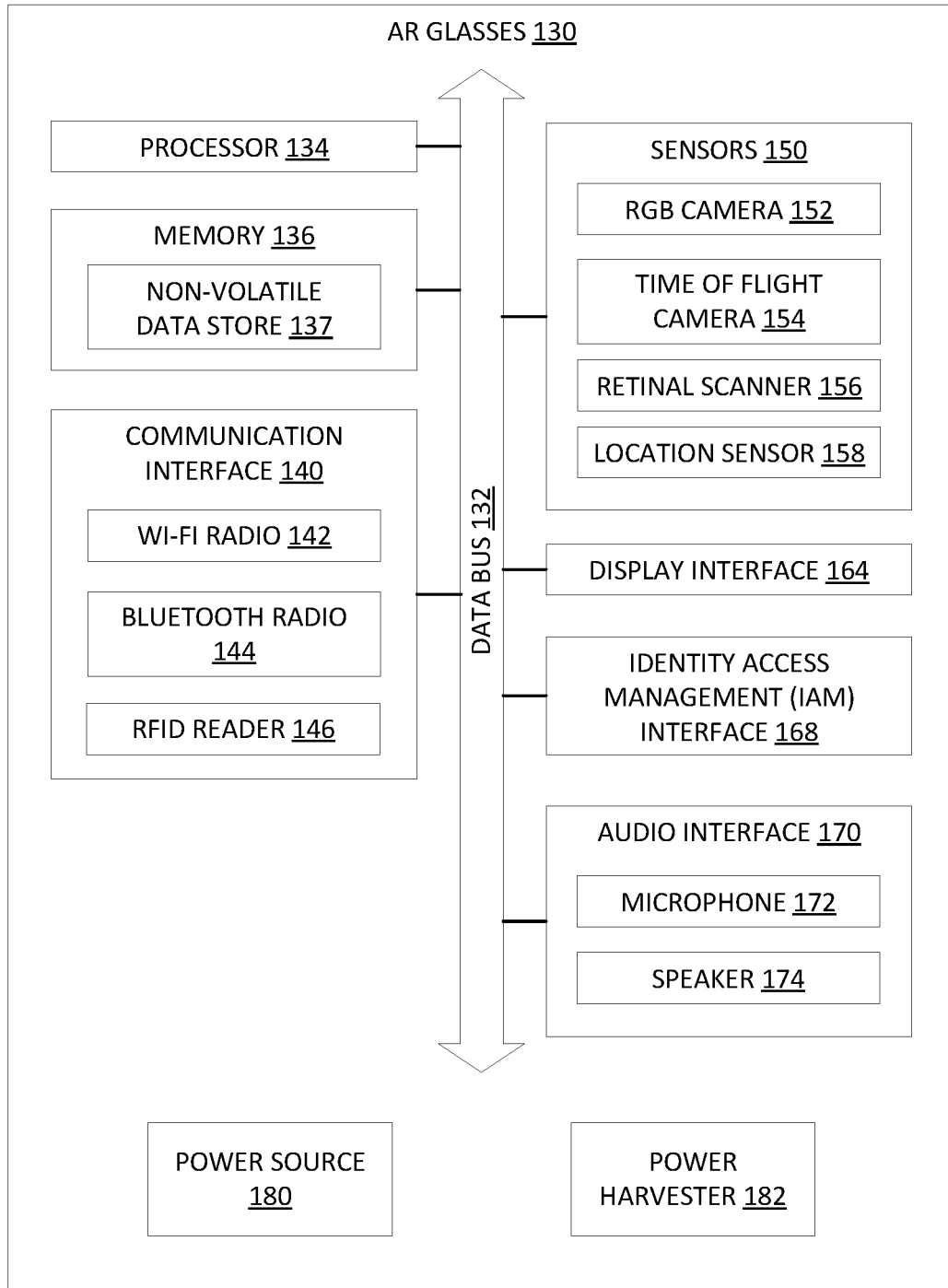
FIG. 2 depicts an example block diagram of an augmented reality device for hands-free medication tracking, according to various aspects of the subject technology.

FIG. 2 depicts an example block diagram of an augmented reality device, or AR glasses 130, for hands-free medication tracking, according to various aspects of the subject technology. AR glasses 130 includes data bus 132, processor 134, memory 136, communication interface 140, sensors 150, display interface 164, identity access management (IAM) interface 168, audio interface 170, power source 180, and power harvester 182. Memory 136 includes non-volatile data store 137. Communication interface 140 includes Wi-Fi radio 142, Bluetooth radio 144, and radio frequency identifier (RFID) reader 146. Sensors 150 include RGB camera 152, time of flight camera 154, retinal scanner 156, and location sensor 158. A location sensor may detect or generate location information identifying a location of the AR glasses 130. Environment sensors may capture (e.g., generate or detect) information about the environment at or near the location of the AR glasses 130. Additional or alternative sensors may be included to detect positioning of the AR glasses 130 such as an accelerometer, a clinometer, or the like. Audio interface 170 includes microphone 172 and speaker 174. The components included in AR glasses 130 are exemplary and other implementations may include a different configuration of components according to use case requirements, power consumption targets, care facility setting, and price point constraints.

AR glasses 130 may include processor 134, which may correspond to any type of general or specialized processor, controller, integrated circuit, application specific integrated circuit (ASIC), field programmable gate array (FPGA), system-on-chip, or similar device, and may include hard-coded circuit elements, firmware, software, or any combination thereof to implement one or more of the specific features describe herein. Processor 134 may communicate with other components of AR glasses 130 via data bus 132, which may comprise one or more communication buses, such as parallel or serial buses.

AR glasses 130 may include memory 136, which may include volatile work memory as well as non-volatile data store 137 for long term data storage. For example, non-volatile data store 137 may comprise flash memory or other memory that retains data after power source 180 is unavailable. When access to network 112 is available, AR glasses 130 may communicate directly with server 114 via network 112. When access to network 112 is unavailable, update messages may instead be written into non-volatile data store 137 that record, for example, user actions with respect to medications or user removal of AR glasses 130. Once access to network 112 is reestablished, AR glasses 130 may send the update messages to server 114. In this manner, AR glasses 130 can adapt to varying levels of network availability.

Communication interface 140 may include one or more wireless radios to communicate with other devices, such as server 114 via network 112. For example, communication interface 140 may include one or more radios, scanners, or other devices that are compliant with Bluetooth and Bluetooth Low Energy (e.g. via Bluetooth radio 144), Near Field Communication (NFC), Wi-Fi (e.g. via Wi-Fi radio 142), contactless Smartcards, Radio-Frequency identification (e.g. via RFID reader 146), ultra-wide band, and other standardized or proprietary protocols. Communication interface 140 may also utilize one or more of sensors 150 for communication, for example by using RGB camera 152 to receive data from scanned 1-D and 2-D barcodes.

Sensors 150 may include one or more sensors to obtain data concerning a surrounding environment of AR glasses 130. RGB camera 152 may include one or more front facing cameras to capture a view corresponding to a gaze of user 110 wearing AR glasses 130. Time of flight camera 154 may include one or more front or rear facing cameras to capture depth information, for example to assist in object detection in conjunction with data received from RGB camera 152, or to assist in user authentication by facial recognition. Retinal scanner 156 may include one or more rear facing cameras to scan one or more eyes of user 110. Retinal scanner 156 is configured to generate a scan that can be used to authenticate the user. For example, biometric information of authorized users may be stored in database 116 and matched to the data from retinal scanner 156 to authorize the user to operate AR glasses 130. According to various implementations, retinal scanner 156 may scan a user's retina and provide processor 134 with information that identifies an orientation of the user's eyes relative to the AR glasses 130. Processor 134 may determine a direction in which the user is gazing relative to the AR glasses 130 or, based on other information processor 134 knows about the current environment, determine on what object or location within the environment the user is looking at. Location sensor 158 may include, for example, a global positioning system (GPS) radio to enable location tracking. Alternatively or additionally, in some implementations, triangulation may be used to determine location, for example by using Wi-Fi or Bluetooth or ultra-wide band signal based triangulation using known networks and/or hubs. Sensors 150 may also include other sensors not shown.

According to various implementations, the AR glasses 130 are configured to perform real time image processing of objects within the purview of camera 152 and/or 154. The image processing may be offloaded to server 114 for detection of objects, or such processing may be performed by the processor 134 of the glasses. The sensors 150 may be dynamically activated to collect data based on a user's workflow. For example, the camera 152 may take an image every 10 seconds. The images may be provided to an image classification algorithm trained to associate an image with one or more likely clinical tasks being performed such as storing a medication, administering an infusion, reviewing fulfillment of a medication order, restocking a medication dispenser, checking patient or room status, or the like. The classification algorithm may provide a probability that the image depicts the associated clinical task. Based on the identified clinical task and, if available, probability, augmentation data may be transmitted to the AR glasses 1130. For example, the system may detect that a user has picked up an object or put down an object. When the object is received into the user's hand, the algorithm may detect the placement and begin identification of the object through image recognition, or by analyzing captured images for identifying features or codes affixed to the object (e.g., barcode or Q-code).

When an item is picked up and/or moved, processor 134 (or server 114) may automatically identify the location from which the item is picked up, and associate an identification of the user wearing the glasses with the movement or placement of the item. The location may be identified using location tracking and/or image recognition, by which captured images are compared against images of known storage locations. When the item is placed in a new location, processor 134 (or server 114) may automatically associate the item with the new location in the database, and create a record indicating that the user placed the item at the new location. In this regard, the record may include a geolocation or shelf or storage identifier, an identifier of the item, and an identifier of the user who placed the item at the new location.

In some implementations, it may be desirable to passively collect data using the AR glasses 130 to generate an inventory map of the care area. The information is passively collected because the user does not need to provide an explicit command to a specific sensor to collect the information. Instead, the AR glasses 130 may automatically trigger the sensors 150 (alone or by command from a central server) to collected the information. The passive collection may be dynamically activated to prioritize resources of the AR glasses 130 for use to augment clinical activities (e.g., those activities impacting patient care) rather than data collection.

As the AR glasses 130 are worn, the sensors 150 may be activated to capture image data or wireless signals. The captured data or signals may be stored in association with location information of the AR glasses 130 at the time the data or signals were captured. The signals may be received from clinical networking equipment (e.g., wireless network access points), medical devices, RFID or other wireless tags affixed to items, or office equipment. The image data may be captured for specific items (e.g., medications, medical equipment), medication dispensers, medical devices (e.g., infusion pump), or physical structures within the clinical area (e.g., signs, floor tiles, doors, trashcans, or other physical landmarks). In some implementations, the AR glasses 130 may provide a prompt to guide a wearer to an area that needs data collection. However, the actual data collection will typically be performed without express user input.

In some implementations, one or more of the sensors 150 may be used to identify when a user is wearing AR glasses 130. For example, retinal scanner 156 may be periodically or continuously engaged to ensure that user 110 is still present and wearing AR glasses 130. The processor associated with the AR glasses 130 may initiate a session when use of the glasses is detected. When retinal scanner 156 is unable to scan a retina or iris of user 110 after a predetermined time threshold, e.g. 1 second, then a determination may be made that user 110 has removed AR glasses 130, thereby ending the previously authorized user session, and AR glasses 130 may send an alert message to e.g. server 114 indicating such a removal. Other methods of confirming a continuous user session may be utilized, such as periodically sending a heartbeat message confirmed by another device of the user, such as a smartphone, smart card, or other token. Since automatic inventory management may rely on user compliance for effective operation, these alert messages may assist in policy enforcement and prevent diversion. For example, the AR glasses 130 may detect (e.g., using image recognition) that the user picked up a controlled medication or substance. If a discontinuity in the session is detected, for example, by the glasses being removed from the user's face for a period of time, an alert message may be sent to the server, or to a device associated with a supervisory function (e.g., the user's supervisor). Further, the alert messages may also provide evidence in forensic investigations, e.g. when investigating medication diversion.

Display interface 164 may drive a display, projector, or other device to show various augmented reality projections to user 110, appearing as overlays on the real environment viewed by user 110. For example, display interface 164 may drive a semi-transparent or transparent display, an image projector projecting through or reflecting off lenses of AR glasses 130, a direct projector of images to the retina, or any other augmented reality display device. The images may be presented to give the perception of being semi-transparent or opaque. The AR projections may include instructions to the user, e.g. administration instructions for a particular medication. Other AR projections may highlight a position of medications for retrieval, for example by providing a high contrast dot, circle, or other visual identifier. Yet other AR projections may identify a position for placement of the medication, such as by identifying a particular compartment or bin in a multi-tiered medication shelf. In this manner, user 110 can quickly and visually identify the correct location for performing a user action with respect to the medication. Additional features for augmented reality graphical user interfaces are described in Schmalstieg and Reitmayer, "The World as a User Interface: Augmented Reality for Ubiquitous Computing" (Central European Multimedia and Virtual Reality Conference) (2005), which is hereby incorporated by reference in its entirety.

Identity access management (IAM) interface 168 may include one or more devices to enable a user to provide credentials for user authentication. In some implementations, a user may be required to authenticate before wearing AR glasses 130. For example, IAM interface 168 may include or interface with one or more biometric scanners, such as a fingerprint sensor, retinal scanner 156, an electrocardiogram (ECG) reader such as a smartwatch, and time of flight camera 154 for facial recognition. IAM interface 168 may also include smartcard readers or other devices to read a contactless smartcard or other unique identifier or token. In some implementations, IAM interface 168 may use communication interface 140 to utilize biometric scanners or readers present on a remote device, such as a tablet or smartphone.

Audio interface 170 may include one or more audio devices, such as microphone 172 and speaker 174. Microphone 172 may enable voice commands to be used, and may also be used as one of sensors 150. Speaker 174 may enable audio prompts, feedback, and alerts to be emitted. Speaker 174 may comprise a piezoelectric speaker, a dynamic speaker, or another type of speaker. For example, different tones may be emitted from the piezoelectric speaker to indicate different states or user prompts. The audio interface 170 (or portion thereof) may be disposed on a portion of an arm of the AR glasses 130 that sit on a user's ear. In this configuration, a user may perceive low volume sounds transmitted or received via the audio interface 170. This can be particularly useful to reduce noise within the care area and provide discreet guidance to the wearer.

Power source 180 provides electrical power for the components of AR glasses 130. Power source 180 may comprise a non-rechargeable battery, a rechargeable battery, a capacitor or super-capacitor, or another energy storage device. Power source 180 may be user accessible and replaceable. To supplement or recharge power source 180, power harvester 182 may be used to receive power from external sources. For example, power harvester 182 may receive wireless power through inductive coils, RF sources, or solar panels. Power harvester 182 may also receive power through direct wired connection, such as via universal serial bus (USB) charging cables, AC-DC chargers, or DC-DC chargers, which may be plugged into an external battery pack or wall mains voltage supply.

Figure 3A:
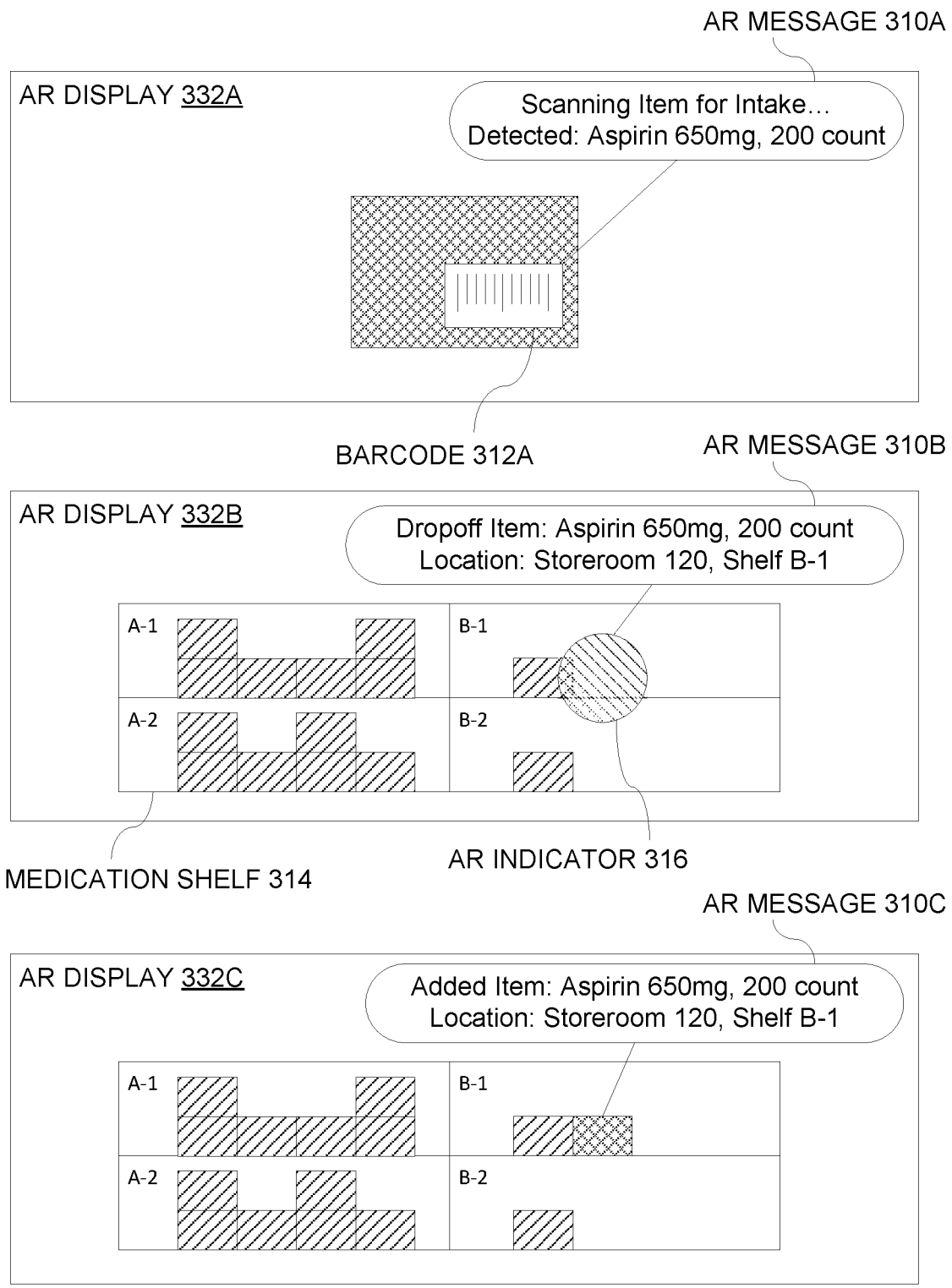
FIG. 3A and FIG. 3B depict various example augmented reality displays of an augmented reality device for hands-free medication tracking, according to various aspects of the subject technology.
Figure 3B:
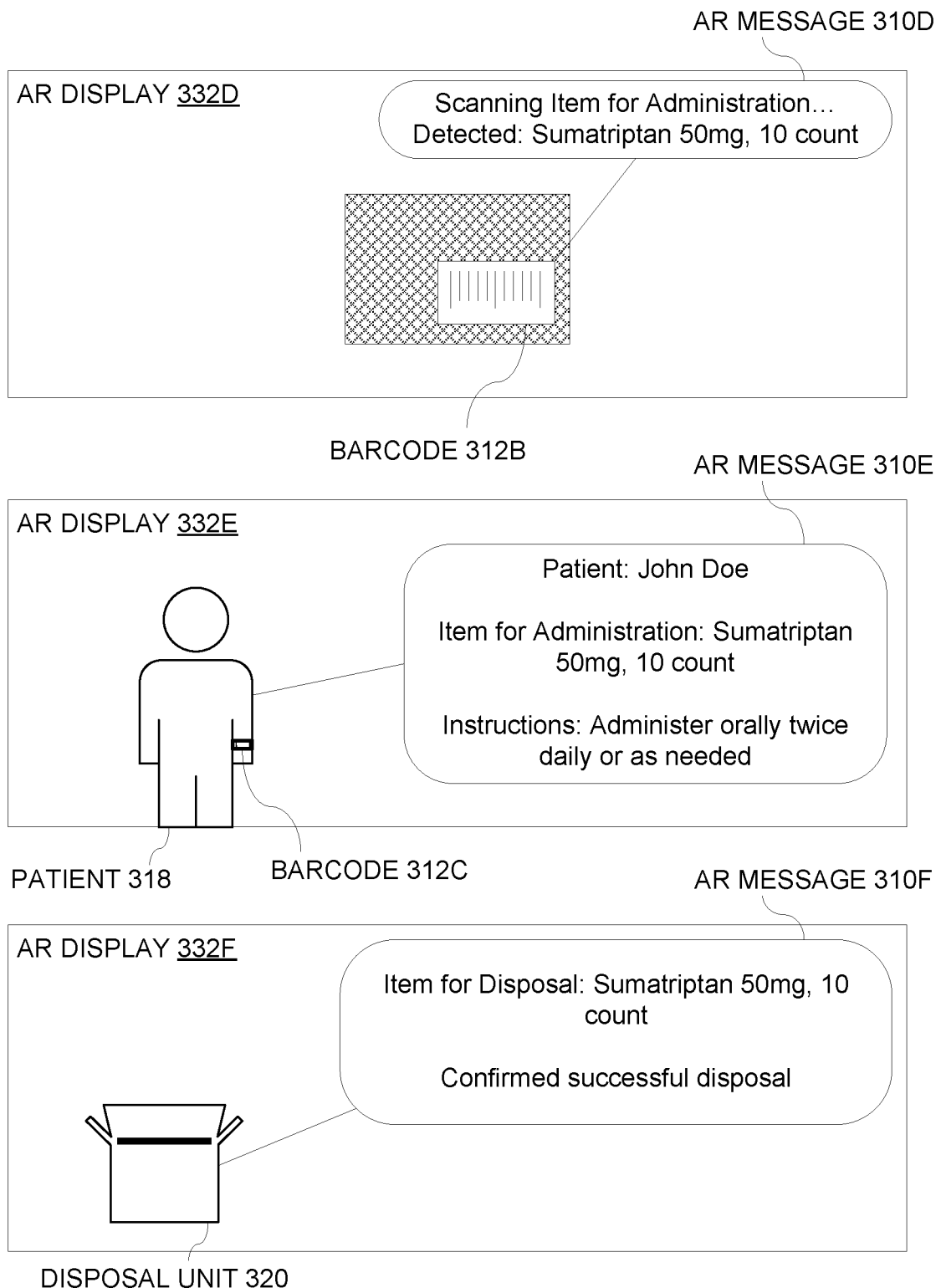

FIG. 3A and FIG. 3B depict various example augmented reality displays of an augmented reality device, such as AR glasses 130, for hands-free medication tracking, according to various aspects of the subject technology. AR glasses 130 is configured to facilitate an intake of medications into a stock room. AR glasses 130 are configured to overlay graphic information regarding inventory control over the real world environment perceived by the user. AR glasses 130 are configured to communicate a location of the user to a server 114, including the user orientation within the current environment and current direction of sight. Visual information may be converted to digital information and sent to the server, which may then use object or image recognition to identify objects and their specific locations within a three-dimensional space within the view of the user. Based on the current location of the user, the system may identify actions that are required to be performed by the user regarding an inventory of medical items. Such actions may include, for example, intake of medication from restock areas, retrieval of medication from specific automated dispensing machines, bins, or shelves, placement or delivery of medication into specific automated dispensing machines, bins, or shelves, administration of a medication to a patient, and disposal of excess medications. The different modes or actions may be triggered based on optical character recognition of information such as a schedule or other electronic medical record. The triggering may be contextual whereby the AR glasses 130 receive an indication to associated with a particular mode. Examples of indications include a specific audio phrase, a movement or gesture of the AR glasses 130 or detected by the AR glasses 130 (e.g., a hand movement or signal), or activation of a button or other physical element on the AR glasses 130. The modes may be predefined or dynamically provided by the system. Each mode may correspond to specific configuration of the AR glasses 130 to allocate resources (e.g., power, processing, network, communications, etc.) efficiently. For example, context and the activity pattern detected for a user may indicate that the user is not working through a specific task. In this case, the AR glasses 130 may enter an alert mode whereby resources are allocated to receiving and processing alert messages at the AR glasses 130. As another example, if the system determines that a user's shift is ended, the AR glasses 130 may adjust resources to a configuration that prioritizes passive data collection. The determination may be based on one or more communications between the AR glasses 130 and a hospital information system such as a time and attendance system.

As one example of an action, an intake worker may have moved from a pharmacy to the stock room to drop off one or more medications. Prior to unloading each medication, the intake worker can simply look at a barcode or other identifier affixed to each medication. Location sensor 158 may detect the current location as being the stock room, and user 110 may be authenticated as the intake worker. Alternatively or additionally, data from sensors 150, such as RGB camera 152 and time of flight camera 154, may be processed through machine learning models trained with visual data of a healthcare facility to determine current locations of objects even without the use of location sensor 158. The machine learning models may be continuously trained based on data from users that wear AR glasses 130. Based on the current location and/or the authenticated user, the user action can be determined, or medication intake in this case. User 110 wearing AR glasses 130 may simply direct gaze towards barcode 312A on a label affixed to the medication, as shown in AR display 332A. AR message 310A may then be projected to the user, indicating the medication is detected as Aspirin 650 mg, 200 count. A corresponding update message may be sent to server 114 to update an inventory of the stock room stored in database 116. For example, a table of inventory records for an associated healthcare facility may be updated with a new record indicating the addition of the 200 count aspirin box to the stock room, and/or a quantity field of an existing aspirin record for the stock room may be updated to reflect the intake of the 200 count aspirin box. Further, fields such as authenticated clinician ID or user ID, patient ID, current location, and other data may also be written for each record, enabling tracking of item movement according to user, patient, location, or other criteria. Thus, user 110 merely needs to look at the medication before drop-off to perform an automatic inventory record update in database 116, which requires no handling of handheld scanners, updating of paperwork, or other burdensome manual processes.

Another example use case is medication drop-off to specific locations, such as bin arrays, medication shelves, and dispensing machines. The user action, or medication drop-off, may be determined based on the detected location (e.g. near a dispensing machine or medication shelf) or authenticated user (e.g. a pharmacist). First, the user may look at a label of the medication for identification, as previously shown in AR display 332A. AR message 310B may then be projected to the user as shown in AR display 332B, indicating to the user where to drop off the medication within medication shelf 314, or "Storeroom 120, Shelf B-1". For example, the data from RGB camera 152 and time of flight camera 154 may be used to build a 3D mapping of the surrounding environment. Database 116 may include a virtual 3D model of medication shelf 314 that includes metadata specifying the preferred positions of particular medications within shelves A-1, B-1, A-2, and B-2. By matching the 3D mapping to the virtual 3D model, the preferred positions for dropping off the identified medication may be determined to position AR indicator 316 and AR message 310B within an AR projection output by display interface 164.

If medication shelf 314 is not in the current view of AR glasses 130, then navigation instructions may be provided in AR messages to direct the user towards the location for drop off. For example, a navigation map showing the user's location and the drop off location may be shown in an AR overlay, and/or step-by-step navigation instructions may be provided, which may also be provided audibly via e.g. speaker 174.

Once medication shelf 314 is in view, an AR indicator 316 may be provided as a visual indicator augmented over the objects (including the shelves) within the user's view, illustrated here as a highlighted circle, although other indicators may be used. In some implementations, the above described 3D model matching to determine the position of the visual indicator may be processed locally on AR glasses 130 to provide the visual indicator as quickly as possible, for example within 1 second or less. Thus, AR glasses 130 may cache and process at least a portion of object and/or image recognition machine learning models from database 116. In implementations where strong connectivity to network 112 is available, then some of the machine learning model processing may be offloaded remotely, e.g. via server 114. Once the medication is placed in the correct location, or shelf "B-1" as shown in AR display 332C, then AR message 310C may be projected to the user to confirm medication drop-off. In some implementations, the drop off may be automatically confirmed based on visual confirmation of the medication being visible on shelf B-1 of medication shelf 314. In some other implementations, the user may provide a voice command, e.g. via microphone 172, to confirm medication drop off. As with the intake process, an update message may be automatically sent to server 114 to update a corresponding table in database 116 to reflect the updated quantity of medications in medication shelf 314.

The above drop-off may proceed similarly for restocking an automated dispensing machine. However, since AR glasses 130 may have previously authenticated user 110, an authentication token may be provided to the automated dispensing machine automatically based on the previous user authentication. The authentication token may be sent by using a RFID transmitter or by using communication interface 140. The automated dispensing machine may receive the authentication token, confirm that the associated user is validated to operate the automated dispensing machine, and accept the authentication token to authorize the user and provide access to the automated dispensing machine for restocking. In this manner, the user can avoid a separate authentication at the automated dispensing machine to facilitate quick and easy restocking while maintaining security.

In some implementations, the AR glasses 130 may detect a medication dispensing cabinet or other medical device within the field of view. In some implementations, the detection may include detecting a user's hand or other indication of a specific device to access. Upon identification of the device to access, the AR glasses 130 may initiate a communication channel with the device to provide biometric data (e.g., iris scan). Once connected, the AR glasses 130 may provide one or more scans to the device. The device may then use the received scan data to verify whether the wearer can access the dispenser. In this way, the dispenser does not need to include an independent biometric scanner and can use a sensor within the AR glasses 130 to verify the user. Although the description here focuses on biometric scanning, other sensors 150 of the AR classes 130 may be used to collect additional or alternative identification/verification data for the user such as an image of the user's palm, a voiceprint, a gesture, or the like.

A retrieval of medications may proceed in a similar fashion. For example, the user might issue a voice command requesting a particular medication for retrieval. Alternatively, the user may use a remote device connected to network 112, such as a tablet or smartphone, to request retrieval of a particular medication. AR glasses 130 may identify a location of the requested medication to be retrieved, and direct the user to the location, e.g. by presenting navigation messages and AR indicators to the user via a projection within the AR glasses 130 or onto the retina of the user. After the user retrieves the medication, an update message may be sent to server 114 to update the inventory in database 116.

Another example use case is administration of medications to a patient. The user action, or medication administration, may be determined based on authenticated user (e.g. a doctor or nurse) or location (e.g. in a patient room). The process may begin with the user directing gaze at barcode 312B in AR display 332D to identify the medication, or "Sumatriptan 50 mg, 10 count". Next, the user may direct gaze at barcode 312C attached to a wrist of the patient to identify patient 318, as shown in AR display 332E. Alternative implementations may use RFID tags or other means of identifying patient 318. AR glasses 130 may then lookup a treatment regimen for patient 318 and provide administration instructions for the user in AR message 310E, which instructs the user to administer orally twice daily or as needed. After confirming administration, an update message may be sent to server 114 to update the inventory in database 116. When administration is for a specific location on patient 318, then the location may also be identified to the user by an AR indicator. For example, if the administration is for an injection, then the AR indicator may identify the position of veins on patient 318. Further features are described in the commonly owned and assigned U.S. patent publication US20150209113A1, entitled "Wearable Electronic Device for Enhancing Visualization during Insertion of an Invasive Device" which is hereby incorporated by reference in its entirety.

In the case where the administration of the medication also involves other medical devices, such as by providing medications via an infusion pump, the medical device may also be programmed accordingly. For example, AR glasses 130 may cause the pumping parameters of the infusion pump to be automatically programmed, thereby avoiding the potentially error prone step of manually entering the parameters by the user. Communication interface 140 may, for example, include a RFID transmitter that can transmit an authentication token based on the authenticated user and the pumping parameters to a RFID reader of the infusion pump. The infusion pump can then verify the authentication token is valid for care of an associated patient identifier, unlock itself for operation by the user, and set the infusion pump parameters automatically for the identified medication. Additionally or in the alternative, AR glasses 130 may identify infusion pump using image recognition and/or through the use of location tracking, and communicate directly with the pump, or with a server connected to the pump, to unlock the pump. In this manner, the user does not have to separately unlock the associated medical device for administration, or the infusion pump in this example, and the parameters are already automatically and correctly programmed, thereby streamlining administration workflows while reducing errors. Depending on facility policy, other communication channels may also be utilized besides RFID.

Another example use case is disposal of excess medications. For example, patient 318 may be discharged early and the entire prescription of Sumatriptan may not be utilized. In this case, it may be important to confirm disposal of excess medications to prevention. As shown in AR display 332F, the disposal might be confirmed by detecting disposal of the medication into an approved container, such as disposal unit 320.

In this manner, each individual inventory change carried out by each user may be recorded and updated in database 116. Each change record may include a detected current location (e.g. via location (e.g., GPS) sensor or machine learning model matching) and a specific location of the user action (e.g. drop off to or retrieval from a specific bin or shelf) when available. Accordingly, the inventory of the healthcare facility can be built up and maintained over time by users wearing AR glasses 130, avoiding the need to perform manual inventory and stock checks. Further, the data gathered by AR glasses 130 can be used to train and refine various machine learning models for recognizing inventory workflow actions and the locations of medications in the healthcare facility. The models can be trained using an initial training period and/or may be continuously trained as users continue to use AR glasses 130 after the initial training period.

The AR glasses 130 may also collect data from one or more of the sensors 150 to validate the disposal. For example, the AR glasses 130 may determine the clinician is performing a waste workflow. As the clinician moves to a wasting station, the AR glasses 130 may collect information to identify the location as an approved wasting station. The AR glasses 130 may cause a message to be transmitted to document the clinician's location at the particular time with the particular wasting need (e.g., the medication). The AR glasses 130 may further track the container including the medication. The tracking may include image captures or wireless signal detection of a tag affixed on the container. This information can be associated with the location of the AR glasses 130 (e.g., time data collected in conjunction with AR glasses 130 location information at the collection time) to indicate where the container has been. The AR glasses 130 may also confirm that the container has been within a field of view to be monitored. Images or other sensor data collected by the AR glasses 130 may be processed by the system to detect whether the container is detected. If the system does not identified the container or the container is not identifiable for a period of time, the AR glasses 130 may cause the AR display to present a prompt to bring the container within a field of sensing for the AR glasses 130. The prompt may include presenting an outline of the container within which the wearer should align the physical container. This can facilitate capture of a clear signal about the container. The system may log the presentation of this prompt to provide an auditable record showing the chain of custody for the container and the wasting protocol.

Figure 4:
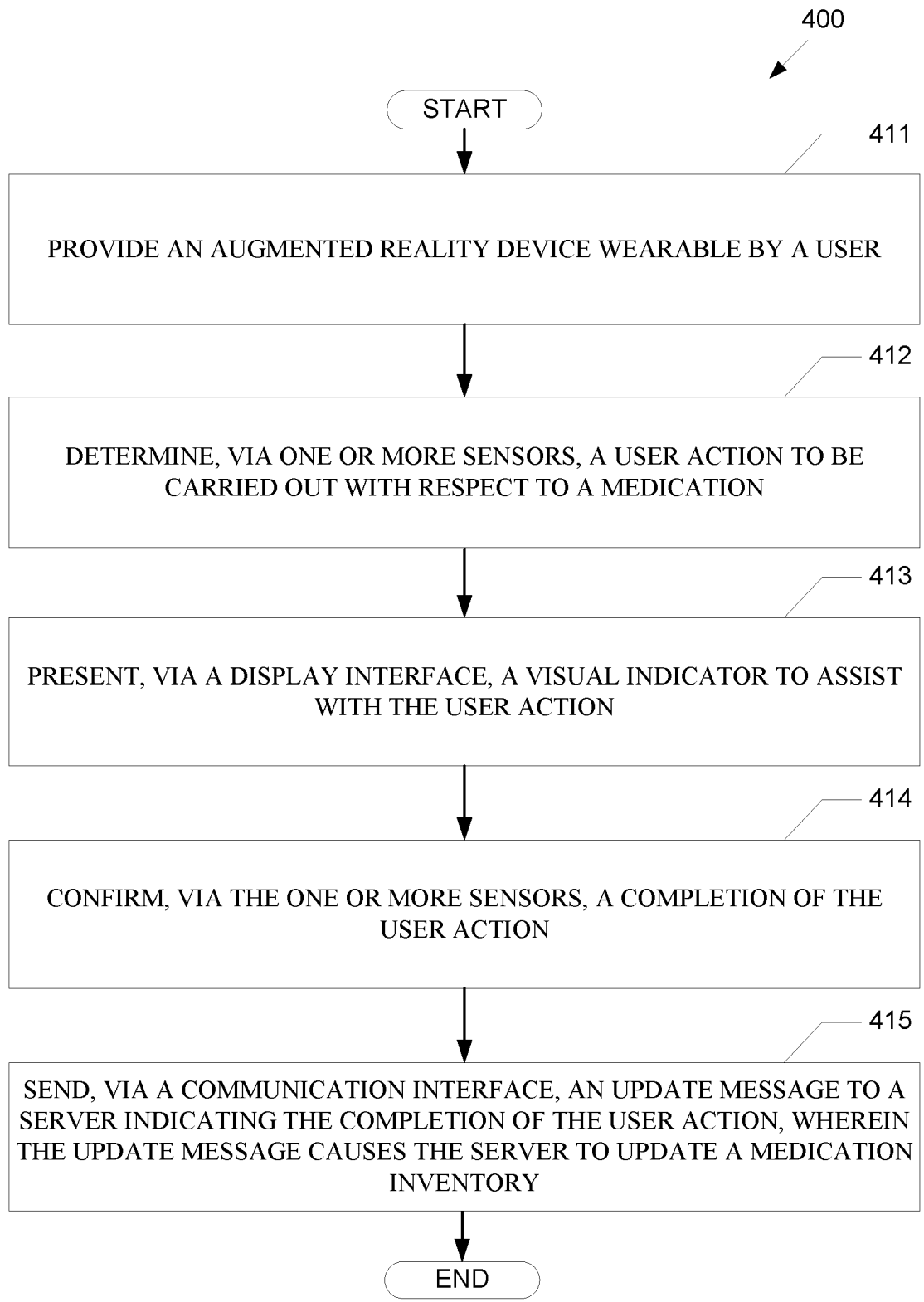
FIG. 4 depicts an example process for using an augmented reality device for hands-free medication tracking, according to various aspects of the subject technology.

FIG. 4 depicts an example process 400 for using an augmented reality device for hands-free medication tracking, according to various aspects of the subject technology. For explanatory purposes, the various blocks of example process 400 are described herein with reference to FIGS. 1-3B, and the components and/or processes described herein. The one or more of the blocks of process 400 may be implemented, for example, by a computing device, including a processor and other components utilized by the device. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, an augmented reality device is provided that is wearable by a user (411). Referring to FIG. 1, this may correspond to providing AR glasses 130 that is wearable by user 110. As discussed above, the augmented reality device may also be a module that is attached to an existing pair of glasses.

Process 400 may continue with determining, using one or more sensors, a user action to be carried out with respect to a medication (412). Referring to FIG. 1 and FIG. 2, this may correspond to processor 134 determining, via sensors 150, a user action to be carried out with respect to medication 120. As discussed with the example use cases above, the determining may be based on the authenticated user (e.g. data from retinal scanner 156), a currently detected location (e.g. data from location sensor 158, RGB camera 152, time of flight camera 154), an intended location for the medication (e.g. data from RGB camera 152 and time of flight camera 154 matched to virtual 3D models in database 116), a patient identification (e.g. from RGB camera 152 or RFID reader 146), or other data from sensors 150 and/or communication interface 140. In some implementations, the data from sensors 150 may be processed through a machine learning model to determine the user action. For example, as discussed above, the data from sensors 150 may be used to generate a 3D mapping of the surrounding environment. The 3D mapping may be generated by processing the data from sensors 150 through a machine learning model trained with model data for medication shelves, bin arrays, automatic dispensing machines, and other locations for retrieving and delivering medications. The 3D mapping may then be matched to virtual 3D models in database 116, wherein the virtual 3D models also specify the positions of particular medications, including preferred positions for drop off. The virtual 3D models may also be specific for containers and dispensers at particular locations, which may also be used to determine a current location when location sensor 158 is unavailable. Thus, by processing the data from sensors 150 through machine learning models, a specific location associated with the user action can be determined.

Process 400 may continue with presenting, via a display interface, a visual indicator to assist with the user action (413). Referring to FIG. 2 and FIGS. 3A-3B, this may correspond to processor 134 presenting, via display interface 164, a visual indicator such as AR messages 310A-310F and AR indicator 316 to assist with the user action. As discussed with the example use cases above, the visual indicator may also include navigation to a specific location of the medication.

Presentation of a visual augmentation may be a general augmentation of the environment. General augmentation may provide general augmentation information about items based on one or more of the user, their role (e.g., pharmacist, pharmacy technician, nurse, doctor, biomedical technician, maintenance, janitorial, etc.), and their location (e.g., physical location within the environment, gaze direction). For general augmentation, the AR glasses 130 may activate one or more of the sensors 150 to receive information about items near the AR glasses 130. The received information may be processed to collect augmentation data about the identifiable items. For example, a janitor in a supply close is not likely to be interested in the location of an ointment but may be interested in the location of cleaning supplies. In this instance, the received information (or augmentation data associated therewith) may be filtered to present the augmentation information most likely to be relevant to the user, their location, and their current activity.

In some implementations, the AR glasses 130 may receive additional input such as a voice command to further define an intended task. For example, if a clinician is detected to be standing in a medical supply closet, it may be unclear what the clinician is attempting to retrieve. At this juncture the AR glasses 130 may display suggestions (e.g., "Are you looking for gauze pads?"). The wearer may speak a command such as, "Find bacitracin." Using the utterance, the AR glasses 130 or speech recognition system associated therewith may determine the user is looking for bacitracin and provide specific augmentation. Once the system determines a specific item or intent, the filtering of augmentation data may exclude augmentation information that does not relate to the specific item or intent. Augmentation data may be associated with specific tasks or items and compared with the specific item or intent for filtering.

In some implementations, it may be desirable to conserve resources of the AR glasses 130 used for sensing and processing signals. One technique to conserve resources is by selectively activating a sensor that is likely to detect the item of interest. For example, if the system determines that a pharmacy technician is retrieving a supply bottle of medication. The bottle may be associated with a specific identifier such as an RFID tag identifier. The AR glasses 130 may broadcast an RFID interrogation signal to detect nearby RFID tags. If a response signal is received corresponding to the tag identifier, the camera may be activated to collect a picture of the environment for augmenting the specific location of the item. The image may be show the specific item and a corresponding augmented reality guidance may be presented to show the location. The guidance may include highlighting or placing a color over the user's field of view corresponding to the location of the specific item.

Process 400 may continue with confirming, via the one or more sensors, a completion of the user action (414). Referring to FIG. 2 and FIG. 3A-3B, this may correspond to processor 134 confirming, via sensors 150, a completion of the user action. For example, the medication may be detected to be placed in a correct location, such as shelf "B-1" in AR display 332C or disposal unit 320 in AR display 332F. In another example, the medication may be detected to be administered to patient, such as patient 318 in AR display 332E.

Process 400 may continue with sending, via a communication interface, an update message to a server indicating the completion of the user action, wherein the update message causes the server to update a medication inventory in a database (415). Referring to FIG. 1 and FIG. 2, this may correspond to processor 134 sending, via communication interface 140, an update message to server 114, via network 112, indicating the completion of the user action. When server 114 receives the update message, server 114 may update a corresponding table in database 116 to reflect the update to the medication inventory.

The features described may be implemented to provide augmented reality workflow or monitoring in different care areas within a medical facility. For example, some medical facilities include a central pharmacy. The central pharmacy may receive orders for medications that are filled by pharmacy technicians. The filling of an order may include identifying the location of a stock container for the medication, counting out the ordered dose (e.g. number of tablets, liquid volume units, inhalers, patches etc.). The filling may include generating a label or other identification for the order. These actions may be detected based on sensor data collected by the AR glasses.

When an order is received, the system may identify pharmacy technicians who are qualified to fill the order and located in the pharmacy. Once identified such as based on information received from AR glasses worn within the pharmacy, augmentation content many be transmitted to a technician to fill the order. The augmentation content may include order information such as the medication to fill, location indicator for the stock bottle, or the like. The user may expressly provide an input to indicate they cannot fulfill the order such as by turning away to start another workflow, blinking, gesturing, speaking a command, or taking another action that can be detected and interpreted by data collected by the AR glasses. As a final step in filling the order, the pharmacy technician may receive augmented reality content directing them to a location to leave the filled order for verification. For example, some orders may require verification by a licensed pharmacist who may also be wearing a pair of AR glasses. The technician's glasses may transmit a signal indicating the order has been placed for verification. The signal may include location information associated with the location where the order was placed. A verification system may then identify an appropriate and available pharmacist within the area to review the order. The identified individual(s) may received augmented reality content indicating the order is awaiting review. The content may include order information or a location identifier to expedite retrieval of the order for review. As the user reaches the order, the AR glasses may receive additional information about the order or the patient. For example, a laboratory result may be received after the order has been filled but before verification. The augmented reality content may alert the reviewing pharmacist of this change and whether it may necessitate a change to the order. One or more of the sensor on the AR glasses worn by the pharmacist may collect data indicating the pharmacist approves the order. The data may include moving the item to a dispatch or approval location. The data may include a gesture or application of a signature.

The detected signature or gesture may be compared to a stored signature or gesture adopted by the pharmacist. In this way, the veracity of the pharmacist's approval may be confirmed when the adopted version corresponds to the version detected.

From the dispatch or approval location, a clinician or other medical worker may bring the filled medication orders to patients or wards for dispensing to the patient. These workers may also be wearing AR glasses. As they approach the dispatch location, the AR glasses may detect that the worker is preparing to make a delivery run through the facility. The AR glasses or other system actor may survey the items waiting delivery and identify a set that maximizes the delivery run by, for example, grouping orders for a similar ward together. This grouping may be presented as augmented reality content when the user looks into the dispatch location. The items to be included on the next run may be highlighted or listed. The AR glasses may also provide routing information as augmented reality content to guide the worker through the facility along an efficient route. An efficient route may be one that, for example, avoids areas being cleaned, avoids backtracking, minimizes elevator rides, etc.

Another example of augmented reality content is to allow a clinician to virtually see into a patient room. In a hospital setting, rest and quite can be very important to a patient's well being and recovery. However, clinicians may need to check the status of life critical items within the patient room such as an infusion pump, vital signs monitoring, patient location (e.g., in the bed or fallen on the floor), etc. Many basic needs can be detected using sensors within the patient room such as a bed weight monitor or other medical device. Using the data from the sensors in the patient room, a virtual image of the room may be generated and presented via the AR glasses. The virtual image may include the position of the patient, vital signs for the patient, historic or future needs for the patient (e.g., current infusion ends in 30 minutes; dinner scheduled for 4:30, etc.). These virtual look-ins can be valuable especially during shift changes when a new set of clinicians may take responsibility for a set of patients. Using a virtual look-in the clinicians do not need to physically open each door and check the critical information they need. The AR glasses may determine the need for virtual look-in when it detects a user's gaze at a patient room door or room number sign near the door. Once detected, the AR glasses may transmit a request for the virtual look-in information and present augmented reality content such as that described.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RANI chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
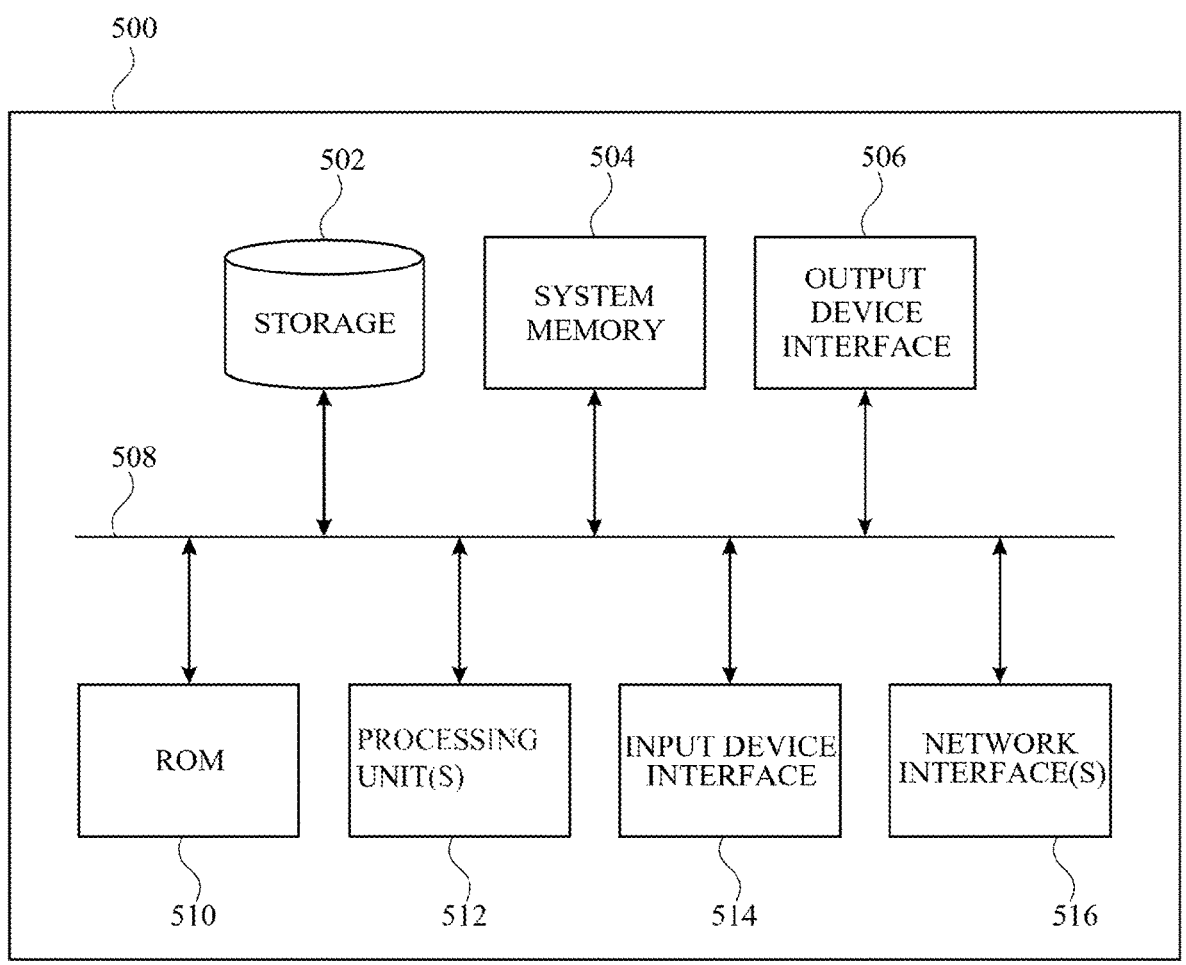
FIG. 5 is a conceptual diagram illustrating an example electronic system for providing an augmented reality device for hands-free medication tracking, according to various aspects of the subject technology.

FIG. 5 is a conceptual diagram illustrating an example electronic system 500 for providing hands-free medication tracking using an augmented reality device, according to various aspects of the subject technology. Electronic system 500 may be a computing device for execution of software associated with one or more portions or steps of process 400, or components and processes provided by FIGS. 1A-4. Electronic system 500 may be representative, in combination with the disclosure regarding FIGS. 1A-4, of the AR glasses 130 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Some implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

Figure 6:
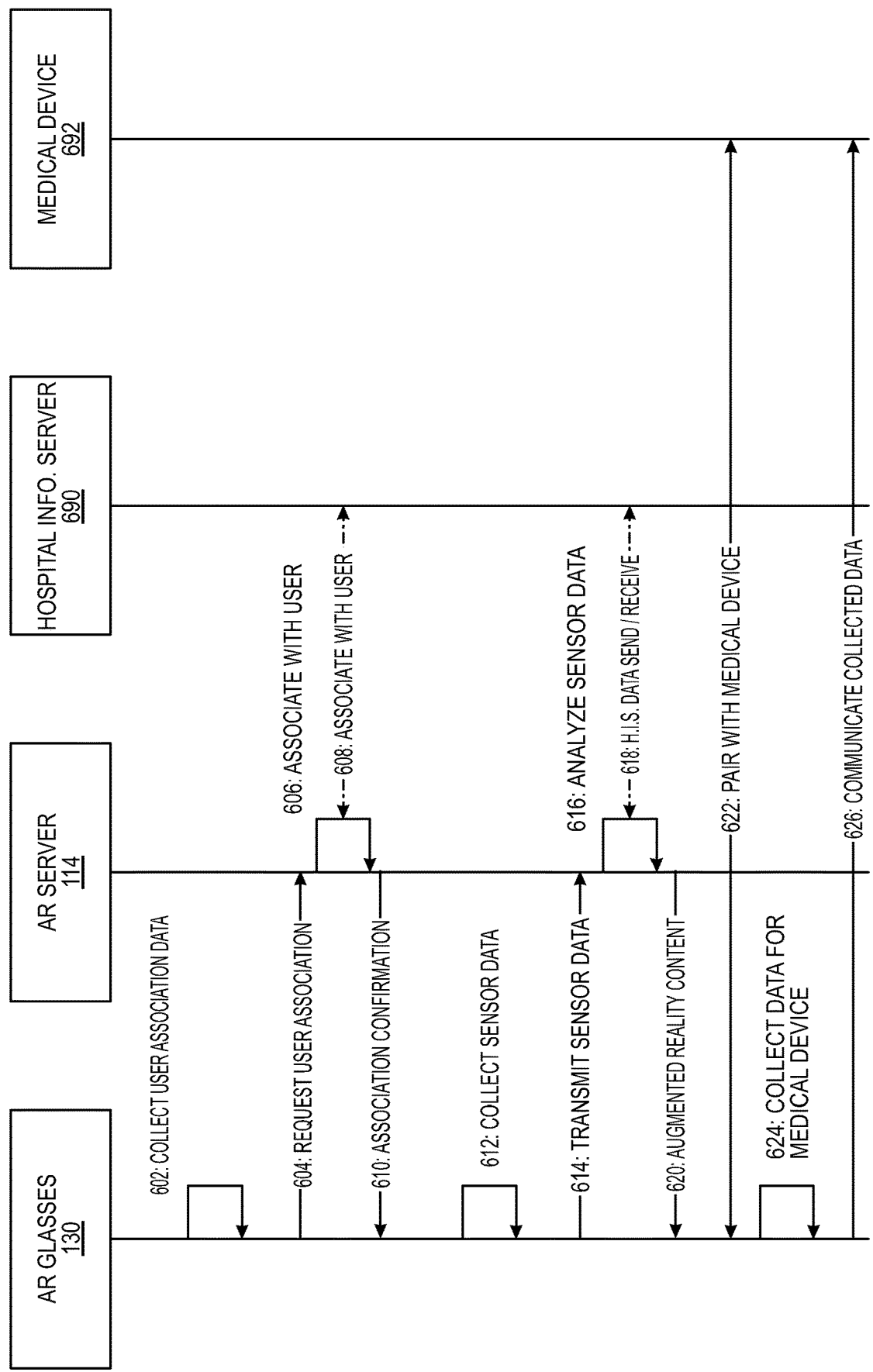
FIG. 6 is an interaction diagram illustrating example communications that may facilitate one or more of the augmented reality features described herein.

FIG. 6 is an interaction diagram illustrating example communications that may facilitate one or more of the augmented reality features described herein, according to various aspects of the subject technology. The message flow of FIG. 6 shows messages exchanged between several entities which can be included in an augmented reality system including a hospital information server 690 (e.g., electronic medical record system, patient information system, laboratory information system, time and attendance system, security system, or the like) and a medical device 692 such as an infusion pump or medication dispensing cabinet. For ease of explanation, the number of entities shown has been limited. However, it will be understood that additional entities can be added or multiple entities combined consistent with the description herein.

Messaging 602 may be performed after the AR glasses 130 are activated or detected to be worn by a user. The activation may be determined based on actuation of a button or pressure sensors within the AR glasses 130 (e.g., detecting the arms resting on a user's ear, nose or other body part) or camera (e.g., detecting a user's iris). Messaging 602 may collect information to associate a user with the AR glasses 130. The collection may include activating one or more sensors of the AR glasses 130 such as the camera (e.g., to capture an image of the user) or wireless sensor (e.g., to capture a wireless signal from, for example, a user badge).

Messaging 604 transmits a request from the AR glasses 130 to the AR server 114 The request may include the information collected via messaging 602. The request may include an identifier for the AR glasses 130 to facilitate unique pairing between the AR glasses 130 and the associated user.

The AR server 114 may perform messaging 606 to associate the user with the AR glasses 130 based at least in part on the information included in the request received via messaging 604. Associating with the user may include verifying the information about the user to ensure the user is authorized to access the system and what level of access is permitted. The association may be stored in a database accessible by the AR server 114. In some implementations, the association may include messaging 608 to send or receive data to complete the association. For example, the hospital information server 690 may be the source of user roles or permissions.

Association with a user may also include identifying initial augmented reality content to present via the AR glasses 130. The identification may be based on analysis of the data sent with the association request. For example, if a nurse requests association while the AR glasses 130 are located in a supply room, the AR server 114 may predict that the nurse is going to be performing inventory work and obtain inventory or other content related to the location. In some implementations, there may be general information to present to the user such as a training reminder or announcement about the medical facility. The analysis may include providing sensor data to a trained machine learning model to identify a task, activity, patient, or device the user may be interacting with.

The AR server 114 may, via messaging 610, transmit an association confirmation to the AR glasses 130. The confirmation may include the augmented reality content. The confirmation may include a token or other value to uniquely identify the association. The token may be included in subsequent messages to confirm and associate communications with the AR glasses 130 and associated user. The confirmation may include configuration information for the AR glasses 130. For example, the AR server 114 may determine a task that may not require images. In this case, the AR glasses 130 may receive configuration information to divert resources from a camera thereby preserving the overall resources available to other components of the AR glasses 130.

The configuration information may additionally or alternatively include configurations for specific sensors such as sample rate, radio power or frequency for wireless scanning, or the like. The AR glasses 130 may present AR content received from the AR server 114.

The sensors of the AR glasses 130 may collect data. Via messaging 614, the AR glasses may transmit the collected data to the AR server 114. The transmission may be triggered by one or more of: a quantity of data collected, location of the AR glasses 130, amount of movement by the AR glasses 130, or other parameter detectable by the AR glasses 130. In some implementations, the data may be transmitted at or near the time of collection to the AR server 114 (e.g, "in real time"). The messaging 614 may include the association token or other identifier to associate the data with the AR glasses 130 and/or user.

The AR server 114 may use messaging 616 to analyze the sensor data received from the AR glasses 130. The analysis may include classifying the images or other data with a machine learning model as described. The analysis may include querying the hospital information server 690 for additional information such as inventory or patient data. The analysis may include storing information in the hospital information server 690 such as dispensing events, inventory counts, witnessing or other verifications, medication administration, or the like. The querying or storing of data at the hospital information server 690 may be performed via messaging 618. The analysis at 616 may include identifying augmented reality content to provide to the AR glasses 130 based on the user, location of the AR glasses 130, and sensor data.

For example, the AR glasses 130 may capture information from a drug to be infused. The AR server 114 may compare the drug to be infused with previous drugs provided to the patient. In some instances, the combination of drugs may have a harmful interaction or the drug may present allergy concerns for the patient. In some instances, the AR server 114 may analyze the collected data for compliance with a medication administration protocol. The protocol may include sequences of events to perform before, during, or after the infusion. The protocol may include acceptable sites for the infusion which can also be confirmed by data collected from the AR glasses 130. Alert information may be provided as AR content for presentation via the AR glasses 130 if a deviation from protocol or safety concern is identified.

The AR server 114 may provide the augmented reality content via messaging 620. After receiving the AR content, the AR glasses 130 may present the AR content. Presenting the AR content may include presenting prepared content via the AR glasses 130 (e.g., displaying text or an image) or converting the AR content received from the AR server 114 to a format displayable by the AR glasses 130. The messaging 620 may include configuration information for the AR glasses 130. As with the configuration information from the messaging 610, the configuration information in the messaging 620 may adjust one or more functions or devices included in the AR glasses 130. The adjustment may be identified as part of the analysis at messaging 616.

In some circumstances, the AR server 114 may determine that the AR glasses 130 are near the medical device 692. As discussed, the system may identify one or more potential actions the wearer of the AR glasses 130 will perform based on, for example, role, location, previous actions, and data collected by the AR glasses 130. In such instances, the augmented reality content in the messaging 620 may include information about the medical device 692. One example is pairing information to allow the AR glasses 130 to communicate with the medical device 692. This may be desirable to, for example, collect login information for the medical device 692 using the AR glasses 130.

Messaging 662 may be performed between the AR glasses 130 and the medical device 692 to pair. Pairing generally refers to establishing a communication path between two or more devices. The messaging 662 may be standards based (e.g., BLUETOOTH like) or proprietary pairing protocol.

After pairing, messaging 624 may collect information for the medical device 692 such as user biometric data, item information, or the like. The specific information needed by the medical device 692 may be identified as part of or after pairing. The collection may include activating one or more sensors of the AR glasses 130 to obtain the data requested by the medical device 692. Messaging 626 may transmit the collected data from the AR glasses 130 to the medical device 692.

As shown in FIG. 6, data is transmitted directly between entities. However, in some implementations, the data may be transmitted via an intermediate server or data store. In such instances, the communication may identify the availability of data and the location of the data (e.g., file name or record identifier). Similarly, the messaging shown in FIG. 6 is illustrated sequentially, but may be performed in a different order. For example, the messaging 612 through 620 may be repeated to continually collect data with the AR glasses 130, analyze the data, and present AR content.

The functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Clause 1. A wearable augmented reality device comprising: a display interface for presenting a graphical user interface including at least one opaque or semi-transparent graphic element; a communication interface; a location sensor for detecting location information identifying a location of the wearable augmented reality device; an environment sensor for capturing information within the location; and a processor configured to: determine, using location information from the location sensor and environment information from the environment sensor, a user action to be carried out with respect to a medication; present, via the display interface, a visual indicator to assist with the user action; confirm, via information received from at least one of the location sensor or the environment sensor, a completion of the user action; and send, via the communication interface, an update message to a server indicating the completion of the user action, wherein the update message causes the server to update a medication inventory in a database.

Clause 2. The wearable augmented reality device of Clause 1, wherein the environment sensor comprises a camera, and wherein the processor is configured to: automatically detect, based on image information received from the camera, when an the medication is picked up by a user currently associated with the augmented reality device; automatically determine, when the medication is picked up from a current location, an identification of the medication based on capturing one or more images of the medication via the camera; and generate a record that indicates a time at which the medication is picked up and moved, and that associates the movement of the medication from the current location with the user currently associated with the augmented reality device.

Clause 3. The wearable augmented reality device of Clause 1 or Clause 2, wherein the environment sensor comprises a retinal scanner, and wherein prior to determining the user action, the processor is configured to: authenticate, via information collected by the retinal scanner, a user for operating the augmented reality device.

Clause 4. The wearable augmented reality device of Clause 3, wherein the processor is configured to determine the user action to be carried out based on a role or a permission associated with the authenticated user.

Clause 5. The wearable augmented reality device of any of Clause 3 or Clause 4, wherein the processor is further configured to: determine that the retinal scanner has not scanned a retina of the user for a predetermined time threshold; and transmit, via the communication interface, an alert message indicating the user removed the augmented reality device.

Clause 6. The wearable augmented reality device of any of Clause 3 through 5, further comprising a second environmental sensor to capture additional information within the location, and wherein the processor is further configured to: detect, based at least in part on second environment information captured by the second environment sensor, a medical device within the location; and transmit, via the communication interface, an authentication token to the medical device after authenticating the user, wherein the medical device uses the authentication token to unlock the medical device for operation by the user.

Clause 7. The wearable augmented reality device of any of the preceding clauses, wherein the processor is further configured to cause a parameter of a medical device to be programmed based on the medication.

Clause 8. The wearable augmented reality device of any of the preceding clauses, wherein the processor is configured to determine the user action to be carried out by processing data from the environment sensor through at least portions of an image recognition machine learning model, wherein the image recognition machine learning model receives a set of image data as an input and provides at least one user action as an output.

Clause 9. The wearable augmented reality device of any of the preceding clauses, wherein the processor is configured to determine the user action to be carried out by processing data from the location sensor through at least portions of a machine learning model, wherein the machine learning model receives a set of data from the location sensor as an input and provides at least one user action as an output.

Clause 10. The wearable augmented reality device of any of the preceding clauses, wherein the processor is configured to: identify a patient based at least in part on one or more of: the environment information and the location information; and determine the user action to be carried based on the patient and the medication.

Clause 11. The wearable augmented reality device of any of the preceding clauses, wherein the wearable augmented reality device further comprises: an accelerometer configured to detect a position of the wearable augmented reality device, and wherein the processor is configured to present the visual indicator based on the position detected by the accelerometer.

Clause 12. The wearable augmented reality device of any of the preceding clauses, wherein the visual indicator comprises an augmented reality projection identifying a position for the user action with respect to the medication within an augmented reality projection that is output by the display interface.

Clause 13. The wearable augmented reality device of any of the preceding clauses, wherein the wearable augmented reality device further comprises: a radio frequency identifier (RFID) reader, and wherein the processor is configured to determine the medication by reading a RFID tag of the medication via the RFID reader.

Clause 14. A method for providing hands-free medication tracking, the method comprising: providing an augmented reality device wearable by a user; determining, using first information received from one or more sensors of the augmented reality device, a user action to be carried out with respect to a medication; presenting, via a display interface of the augmented reality device, a visual indicator to assist with the user action; confirming, via second information received from the one or more sensors of the augmented reality device, a completion of the user action; and transmitting, via a communication interface of the augmented reality device, an update message to a server indicating the completion of the user action, wherein the update message causes the server to update a medication inventory in a database.

Clause 15. The method of Clause 14, wherein the one or more sensors include a retinal scanner, and wherein prior to the determining, the method further comprises: authenticating, via information collected by the retinal scanner, a user wearing the augmented reality device.

Clause 16. The method of Clause 15, wherein determining the user action to be carried out is based on a role or a permission of the authenticated user.

Clause 17. The method of Clause 15 or Clause 16, wherein the method further comprises: determining that the retinal scanner has not scanned a retina of the user for a predetermined time threshold; and transmitting, via the communication interface, an alert message indicating the user removed the augmented reality device.

Clause 18. The method of any of Clauses 14 through 17, further comprising: causing a parameter of a medical device to be programmed based on the medication.

Clause 19. The method of any of Clauses 14 through 18, wherein the visual indicator comprises an augmented reality projection identifying a position for the user action with respect to the medication within an augmented reality projection that is output by the display interface.

Clause 20. A non-transitory storage medium comprising instructions that, when read by one or more processors, cause a method comprising: determining, using one or more sensors of an augmented reality device, a user action to be carried out with respect to a medication; presenting, via a display interface of the augmented reality device, a visual indicator to assist with the user action; confirming, via the one or more sensors of the augmented reality device, a completion of the user action; and sending, via a communication interface of the augmented reality device, an update message to a server indicating the completion of the user action, wherein the update message causes the server to update a medication inventory in a database.

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Further Consideration:

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML, document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Aspects described include artificial intelligence or other operations whereby the system processes inputs and generates outputs with apparent intelligence. The artificial intelligence may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired item location. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine-readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A wearable augmented reality device comprising:
    a display interface for presenting a graphical user interface including at least one opaque or semi-transparent graphic element;
    a communication interface;
    a location sensor for detecting location information identifying a location of the wearable augmented reality device;
    an environment sensor for capturing information associated with a surrounding environment of the wearable augmented reality device within the location; and
    a processor configured to:
        determine, using location information from the location sensor and environment information from the environment sensor, that a user currently associated with the augmented reality device is near a storage location for a user action that includes drop off or retrieval of a medication;
        determine a preferred position for the medication in the storage location based on a three-dimensional model of the surrounding environment and a virtual model of the storage location;
        present, via the display interface, a visual indicator augmented over objects in the storage location within the user's view to assist the user with dropping off or retrieving the medication at the preferred position by highlighting the preferred position within the storage location and among the objects in the storage location;
        confirm, via information received from the environment sensor, that the drop off or retrieval of the medication was completed; and
        send, via the communication interface based on confirming that the drop off or retrieval of the medication was completed, an update message to a server indicating the completion of the user action, wherein the update message causes the server to update a medication inventory in a database.

2. The wearable augmented reality device of claim 1, wherein the environment sensor comprises a camera, and wherein the processor is configured to:
    automatically detect, based on image information received from the camera, when the medication is picked up by the user currently associated with the augmented reality device;
    automatically determine, when the medication is picked up from a current location, an identification of the medication based on capturing one or more images of the medication via the camera; and
    generate a record that indicates a time at which the medication is picked up and moved, and that associates the movement of the medication from the current location with the user currently associated with the augmented reality device.

3. The wearable augmented reality device of claim 1, wherein the environment sensor comprises a retinal scanner, and wherein prior to determining the user action, the processor is configured to:
    authenticate, via information collected by the retinal scanner, the user for operating the augmented reality device.

4. The wearable augmented reality device of claim 3, wherein the processor is configured to determine the user action to be carried out based on a role or a permission associated with the authenticated user.

5. The wearable augmented reality device of claim 3, wherein the processor is further configured to:
    determine that the retinal scanner has not scanned a retina of the user for a predetermined time threshold; and
    transmit, via the communication interface, an alert message indicating the user removed the augmented reality device.

6. The wearable augmented reality device of claim 3, further comprising a second environmental sensor to capture additional information within the location, and
    wherein the processor is further configured to:
    detect, based at least in part on second environment information captured by the second environment sensor, a medical device within the location; and
    transmit, via the communication interface, an authentication token to the medical device after authenticating the user, wherein the medical device uses the authentication token to unlock the medical device for operation by the user.

7. The wearable augmented reality device of claim 1, wherein the processor is further configured to cause a parameter of a medical device to be programmed based on the medication.

8. The wearable augmented reality device of claim 1, wherein the processor is configured to determine the user action to be carried out by processing data from the environment sensor through at least portions of an image recognition machine learning model, wherein the image recognition machine learning model receives a set of image data as an input and provides at least one user action as an output.

9. The wearable augmented reality device of claim 1, wherein the processor is configured to determine the user action to be carried out by processing data from the location sensor through at least portions of a machine learning model, wherein the machine learning model receives a set of data from the location sensor as an input and provides at least one user action as an output.

10. The wearable augmented reality device of claim 1, wherein the processor is configured to:
identify a patient based at least in part on one or more of: the environment information and the location information; and
determine the user action to be carried based on the patient and the medication.

11. The wearable augmented reality device of claim 1, wherein the wearable augmented reality device further comprises:
an accelerometer configured to detect a position of the wearable augmented reality device, and wherein the processor is configured to present the visual indicator based on the position detected by the accelerometer.

12. The wearable augmented reality device of claim 1, wherein the visual indicator comprises an augmented reality projection identifying a position for the user action with respect to the medication within an augmented reality projection that is output by the display interface.

13. The wearable augmented reality device of claim 1, wherein the wearable augmented reality device further comprises:
a radio frequency identifier (RFID) reader, and wherein the processor is configured to determine the medication by reading a RFID tag of the medication via the RFID reader.

14. A method for providing hands-free medication tracking, the method comprising:
providing an augmented reality device wearable by a user;
capturing, with one or more sensors of the augmented reality device, information associated with a surrounding environment of the augmented reality device;
determining, using the information received from the one or more sensors of the augmented reality device, that the user is near a storage location for a user action that includes drop off or retrieval of a medication;
determining a preferred position for the medication in the storage location based on a three-dimensional model of the surrounding environment and a virtual model of the storage location;
presenting, via a display interface of the augmented reality device, a visual indicator augmented over objects in the storage location within the user's view to assist the user with dropping off or retrieving the medication at the preferred position by highlighting the preferred position within the storage location and among the objects in the storage location;
confirming, via second information received from the one or more sensors of the augmented reality device, that the drop off or retrieval of the medication was completed; and
transmitting, via a communication interface of the augmented reality device based on confirming that the drop off or retrieval of the medication was completed, an update message to a server indicating the completion of the user action, wherein the update message causes the server to update a medication inventory in a database.

15. The method of claim 14, wherein the one or more sensors include a retinal scanner, and wherein prior to the determining, the method further comprises:
authenticating, via information collected by the retinal scanner, a user wearing the augmented reality device.

16. The method of claim 15, wherein determining the user action to be carried out is based on a role or a permission of the authenticated user.

17. The method of claim 15, wherein the method further comprises:
determining that the retinal scanner has not scanned a retina of the user for a predetermined time threshold; and
transmitting, via the communication interface, an alert message indicating the user removed the augmented reality device.

18. The method of claim 14, further comprising:
causing a parameter of a medical device to be programmed based on the medication.

19. The method of claim 14, wherein the visual indicator comprises an augmented reality projection identifying a position for the user action with respect to the medication within an augmented reality projection that is output by the display interface.

20. A non-transitory storage medium comprising instructions that, when read by one or more processors, cause the one or more processors to perform a method comprising:
capturing, with one or more sensors of an augmented reality device worn by a user, information associated with a surrounding environment of the augmented reality device;
determining, using the information received from the one or more sensors of the augmented reality device, that the user is near a storage location for a user action that includes drop off or retrieval of a medication;
determining a preferred position for the medication in the storage location based on a three-dimensional model of the surrounding environment and a virtual model of the storage location;
presenting, via a display interface of the augmented reality device, a visual indicator augmented over objects in the storage location within the user's view to assist the user with dropping off or retrieving the medication at the preferred position by highlighting the preferred position within the storage location and among the objects in the storage location;
confirming, via second information received from the one or more sensors of the augmented reality device, that the drop off or retrieval of the medication was completed; and
transmitting, via a communication interface of the augmented reality device based on confirming that the drop off or retrieval of the medication was completed, an update message to a server indicating the completion of the user action, wherein the update message causes the server to update a medication inventory in a database.

\* \* \* \* \*